(12) United States Patent
Baumann et al.

(10) Patent No.: US 7,914,737 B2
(45) Date of Patent: Mar. 29, 2011

(54) MULTI-LEVEL DIAGNOSTIC APPARATUS WITH A LIFT SYSTEM

(75) Inventors: Renato Baumann, Steinhausen (CH);
Roland Bernet, Immensee (CH); Eric Misselwitz, Stallikon (CH); Andreas Portmann, Mannedorf (CH); Ulrich Schlapfer, Bern (CH); Rolf Schneebeli, Mettmenstetten (CH); Reto Schorno, Adligenswil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 345 days.

(21) Appl. No.: 11/167,417

(22) Filed: Jun. 27, 2005

(65) Prior Publication Data

US 2006/0002820 A1    Jan. 5, 2006

(30) Foreign Application Priority Data

Jul. 1, 2004   (EP) ..................................... 04015548

(51) Int. Cl.
*G01N 21/00* (2006.01)
(52) U.S. Cl. ........... 422/63; 422/500; 422/501; 436/180
(58) Field of Classification Search .................. 422/63, 422/500–501; 436/180
See application file for complete search history.

(56) References Cited

U.S. PATENT DOCUMENTS

| | | | | |
|---|---|---|---|---|
| 5,125,240 A | * | 6/1992 | Knippscheer et al. | .......... 62/266 |
| 5,158,895 A | * | 10/1992 | Ashihara et al. | .............. 436/526 |
| 5,290,708 A | | 3/1994 | Ashihara et al. | |
| 5,370,215 A | | 12/1994 | Markin et al. | ............. 198/346.1 |
| 5,482,839 A | | 1/1996 | Ashihara et al. | |
| 5,529,166 A | * | 6/1996 | Markin et al. | ................ 198/349 |
| 6,228,636 B1 | * | 5/2001 | Yahiro et al. | ............... 435/303.1 |
| 2001/0046689 A1 | * | 11/2001 | Yahiro | ............................ 435/29 |
| 2003/0215357 A1 | | 11/2003 | Malterer et al. | ................ 422/50 |

FOREIGN PATENT DOCUMENTS

| | | |
|---|---|---|
| EP | 0 351 998 B1 | 1/1990 |
| EP | 0 449 321 B1 | 10/1991 |
| EP | 0 990 906 A1 | 4/2000 |
| EP | 1 032 839 B1 | 9/2000 |
| EP | 1272966 A1 | 1/2003 |
| EP | 04015548.3 | 12/2004 |
| EP | 1275966 B1 | 7/2006 |
| JP | 2001074750 A | 3/2001 |
| JP | 200234912 A | 11/2002 |

* cited by examiner

*Primary Examiner* — Jyoti Nagpaul
(74) *Attorney, Agent, or Firm* — Charles M. Doyle; Vivien Banholzer; M. Reza Savari

(57) ABSTRACT

A new multi-level apparatus is disclosed for high throughput processing of samples. The apparatus does not need interruptions for reloading disposables.

10 Claims, 8 Drawing Sheets

MULTI-LEVEL DIAGNOSTIC APPARATUS WITH A LIFT SYSTEM

BACKGROUND OF THE INVENTION

This application claims the benefit of priority under 35 U.S.C. §119 of EP Application 04015548.3, filed Jul. 1, 2004, the contents of which are hereby incorporated by reference.

FIELD OF THE INVENTION

The present invention is directed to an apparatus for conducting an analytical process and a method for performing an analytical process. The invention can be used particularly advantageously in the field of automated analysis, for example in health care.

DESCRIPTION OF RELATED ART

Apparatus for conducting multi-step analytical processes have been known. In EP 1 032 839 there is disclosed an instrument providing handling units for different handling steps on a joint working area. However, future laboratories will have a need to employ high throughput instruments, i.e. instruments which can handle analysis of many samples in parallel. Analyses usually require the use of disposables, i.e. vessels or containers that are designed to contain the sample through one or more analytical steps. Thus, in high throughput analyses, a large number of disposables are needed. High throughput of samples further requires the storage of many disposables. Therefore, throughput of known instruments was limited. Therefore, there was a particular need for instruments, which allow high throughput analyses. This object is solved by the present invention.

SUMMARY OF THE INVENTION

The first subject of this invention is an apparatus for conducting an analytical process comprising
  a transfer module,
  a plain for storage of disposables and
  a plain for processing samples within said disposables,
  wherein said transfer module is an elevator for transporting said disposables from said plain for storage to said plain for processing.
Another subject of the invention is a method for analysis of a sample in an instrument comprising
  providing a disposable on a first plain,
  transporting said disposable within said first plain to a transfer position,
  transferring said disposable to a second plain, and
  processing said disposable in said second plain.
One possible advantage of present invention is that it eases high throughout analyses.

DETAILED DESCRIPTION OF THE INVENTION

Figure 1:
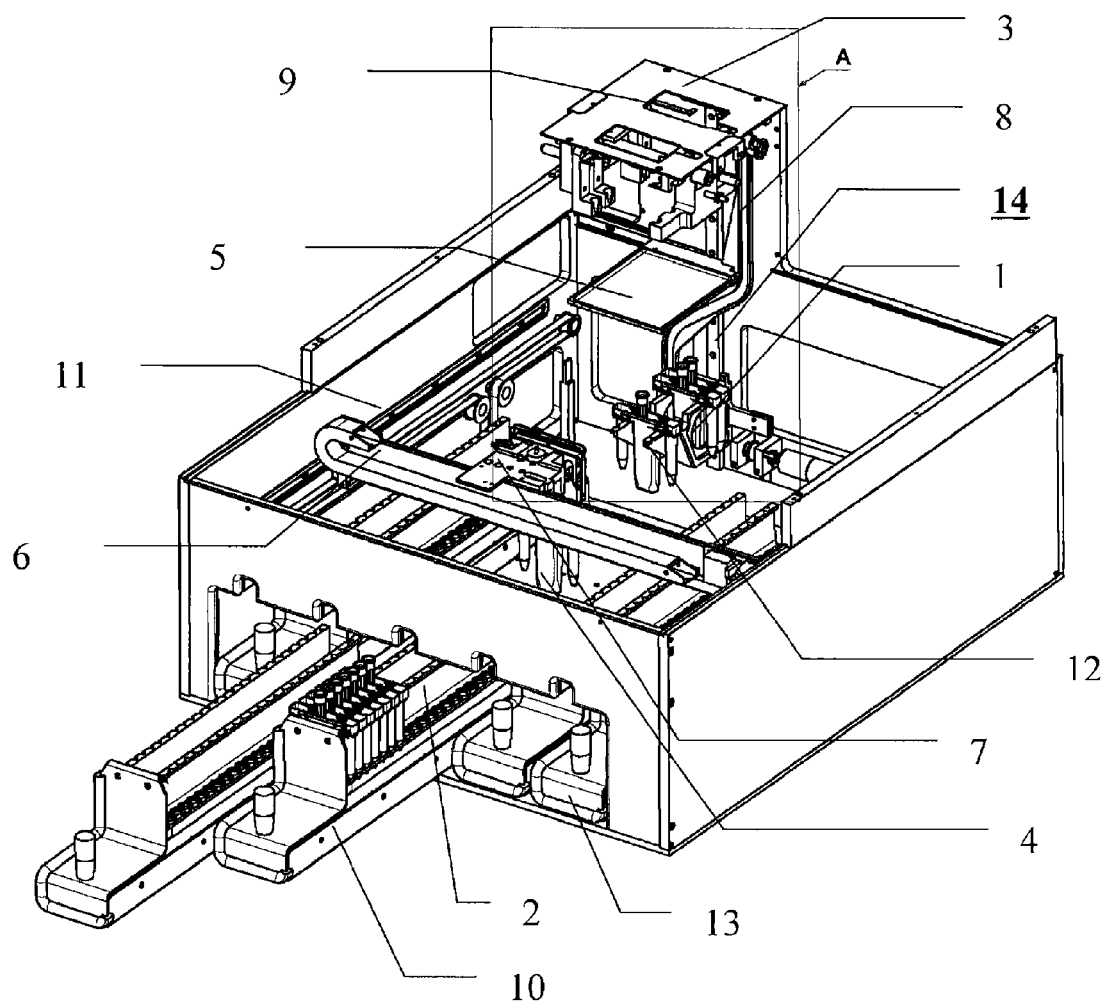
FIG. 1 shows the lift module of the apparatus from front and right hand side. A cut-out position is shown as A.
Figure 2:
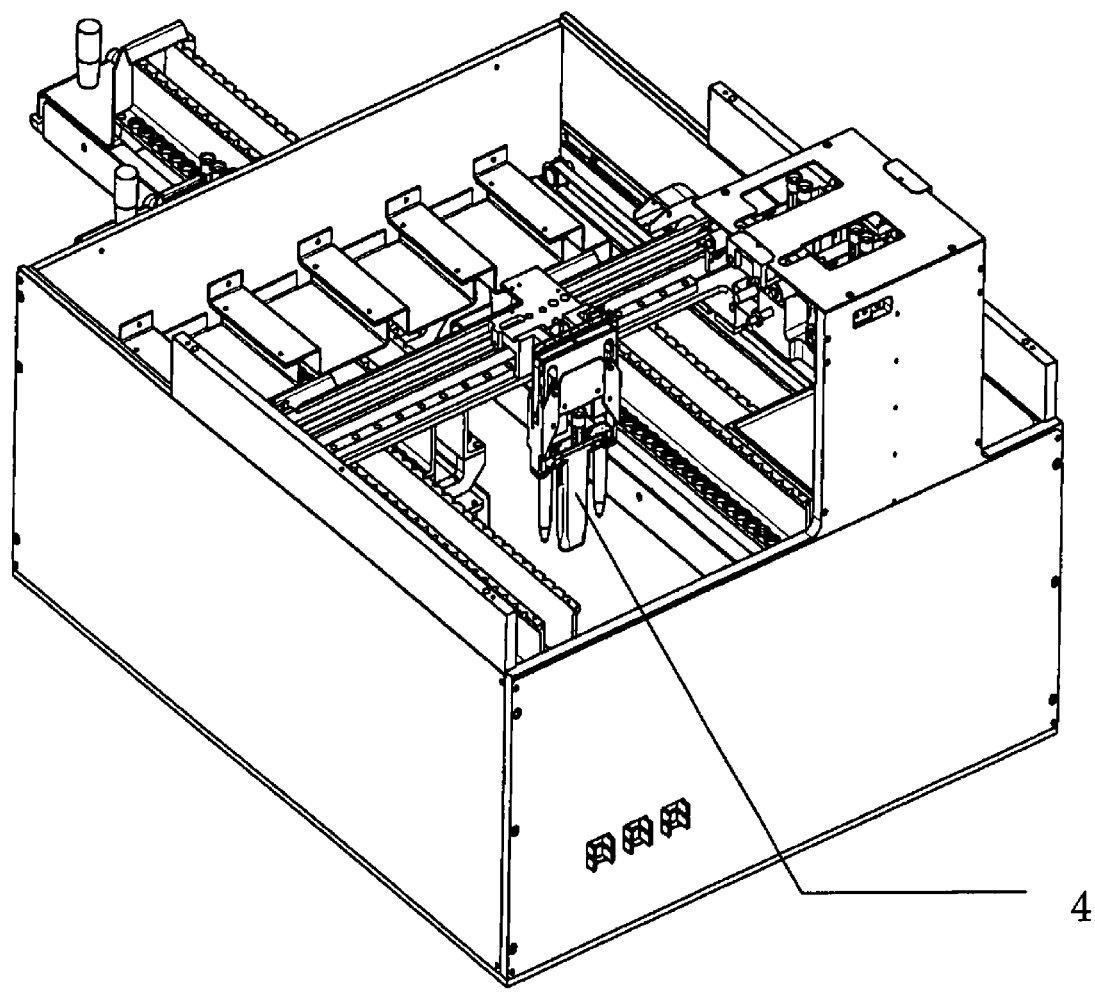
FIG. 2 shows the lift module of the apparatus from back and right hand side.
Figure 3:
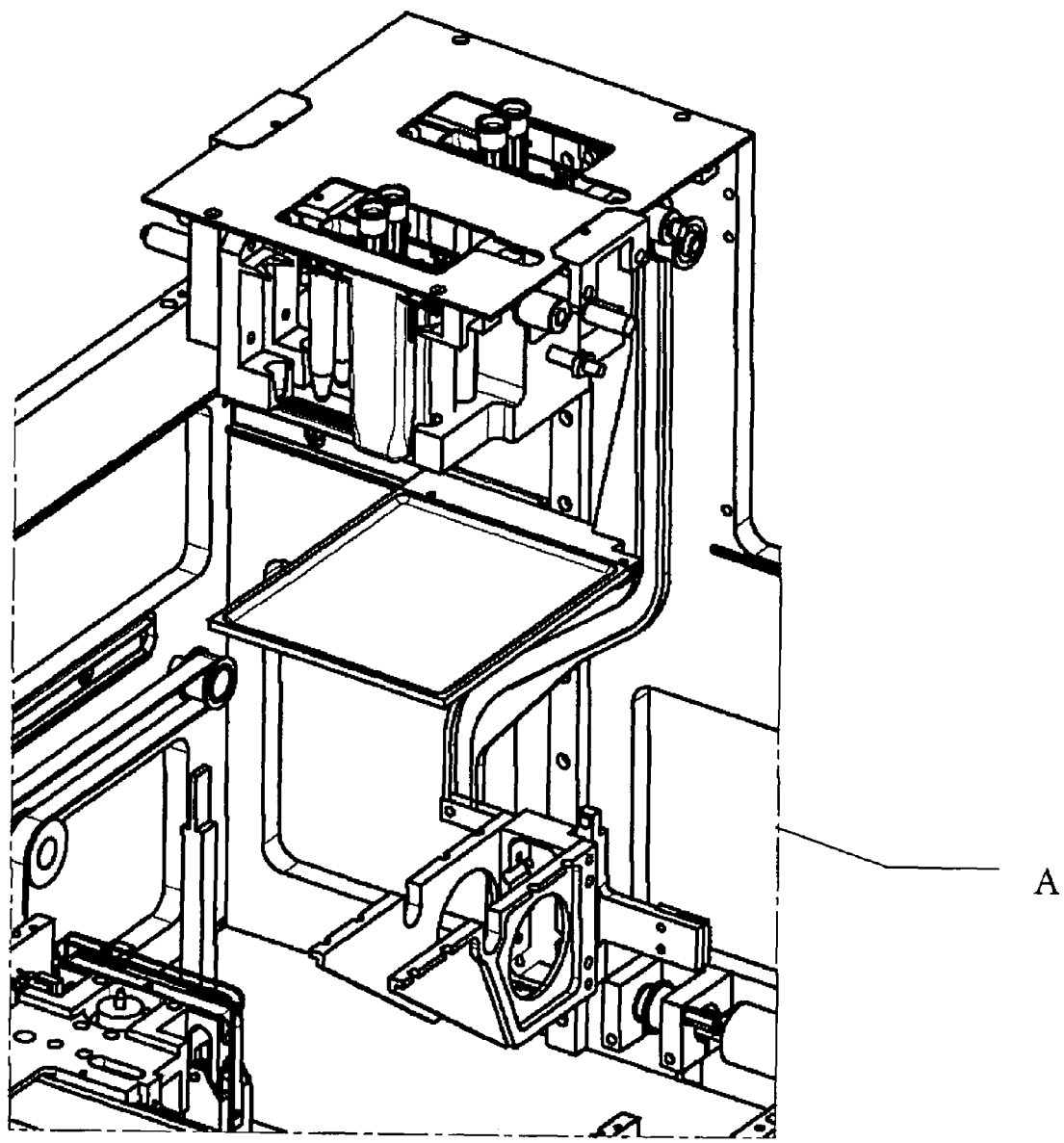
FIG. 3 shows cut-out A of the lift module in the status where the disposables (4) are placed in the upper plain, a shutter (5) has closed the channel and the transfer module is ready for receiving disposables (4).
Figure 4:
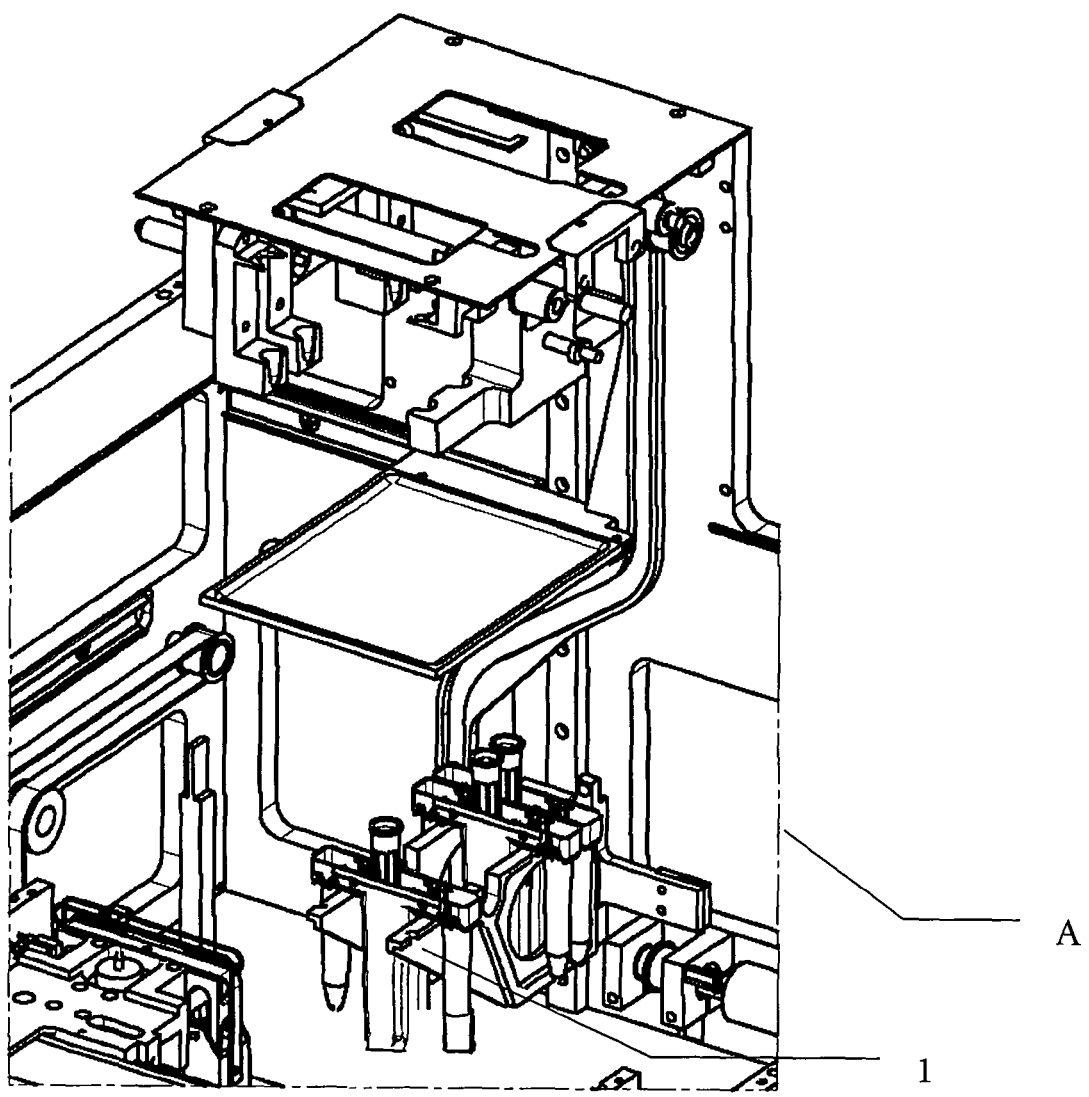
FIG. 4 shows cut-out A of the lift module in the status where three disposables (4) are placed in the transfer module, the disposable input position (9) on the second plain is empty, the shutter is closed and the transfer module is ready for receiving another disposable.
Figure 5:
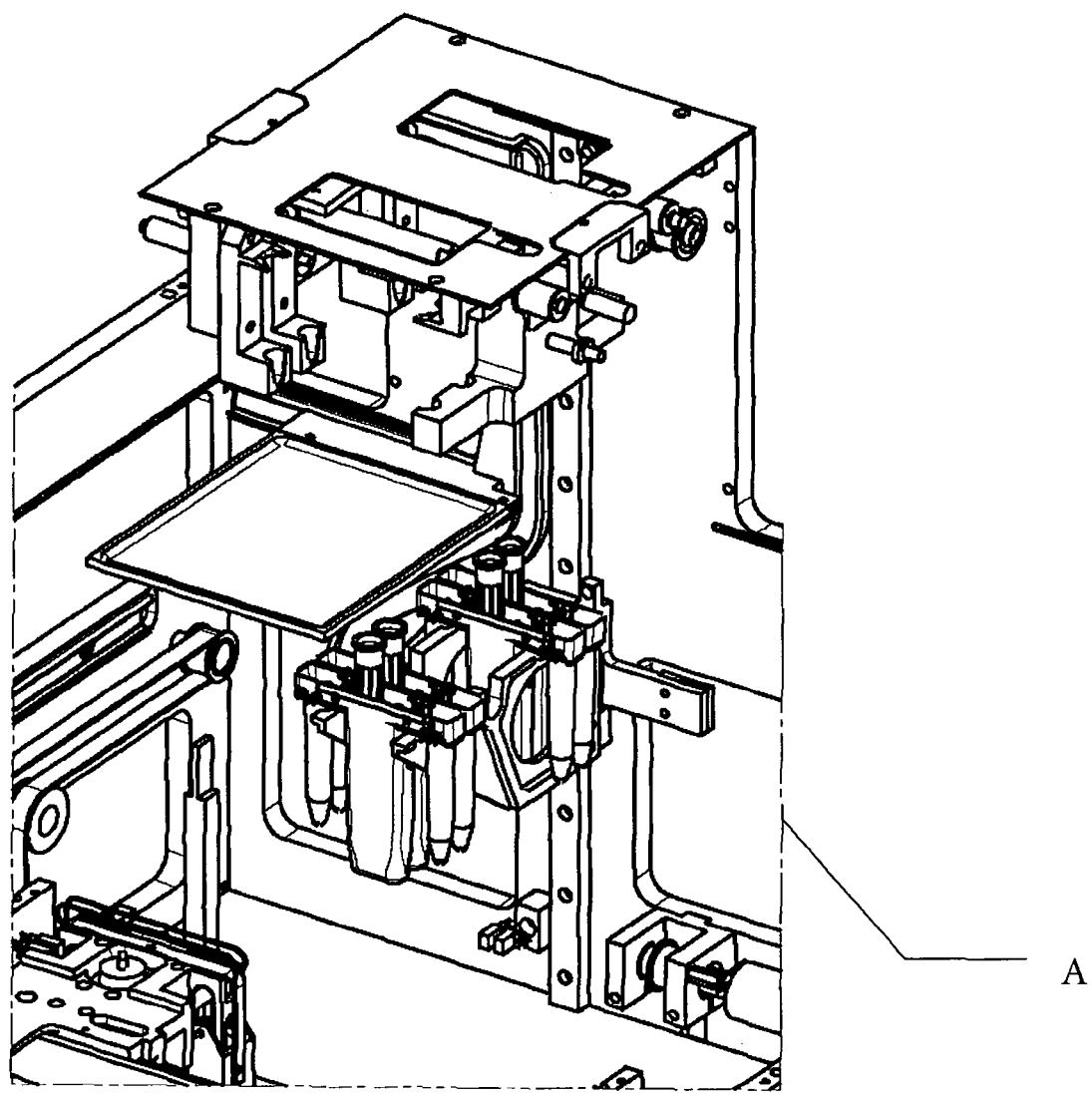
FIG. 5 shows cut-out A of the lift module in the status where four disposables (4) are placed in the transfer module, the disposable input position (9) on the second plain is empty, the shutter is opening and the transfer module is moving towards the input position on the second plain.
Figure 6:
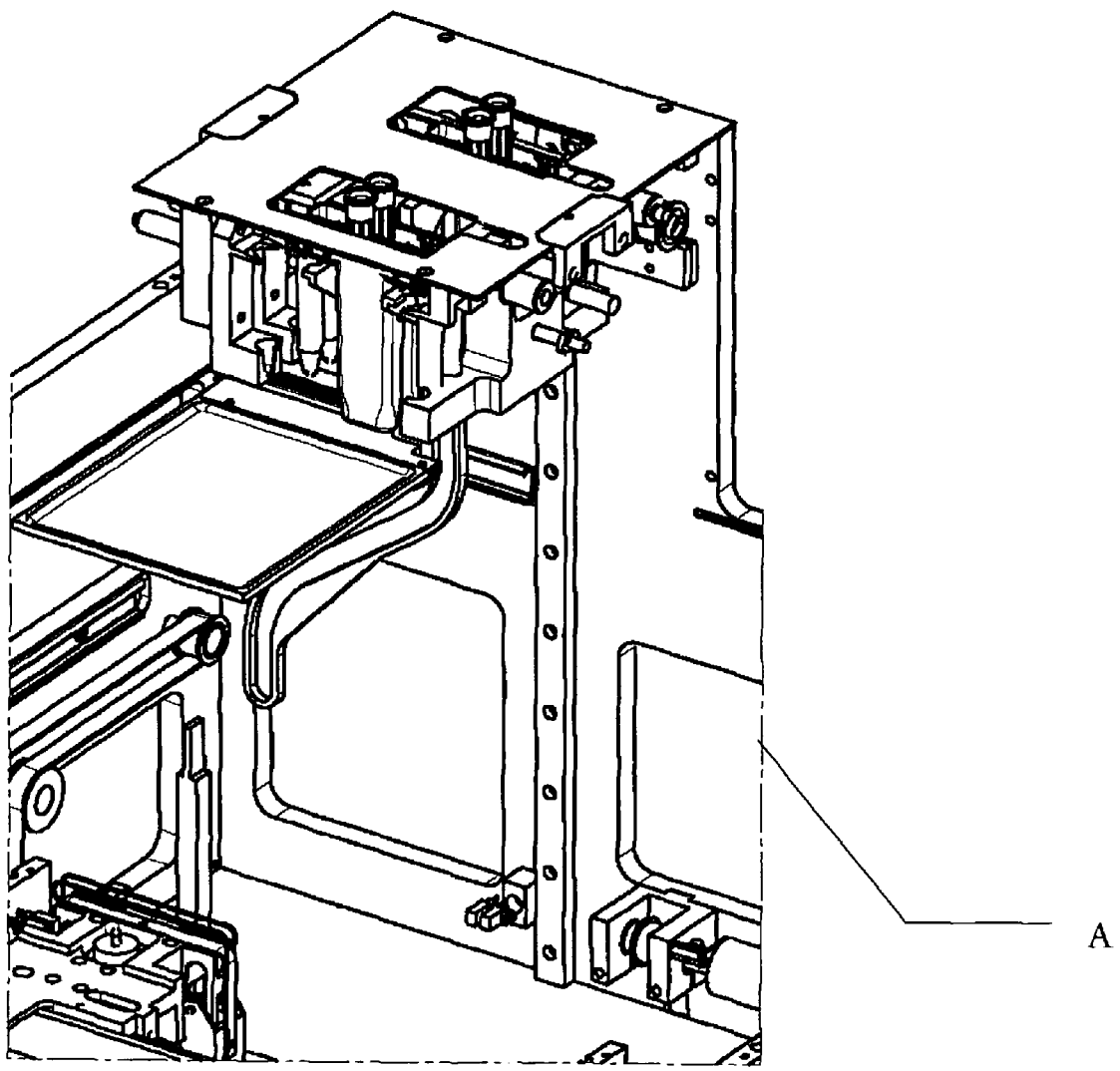
FIG. 6 shows cut-out A of the lift module in the status where four disposables (4) are placed in the transfer module, the transfer module has reached the input position on the second plain, the shutter is still open.
Figure 7:
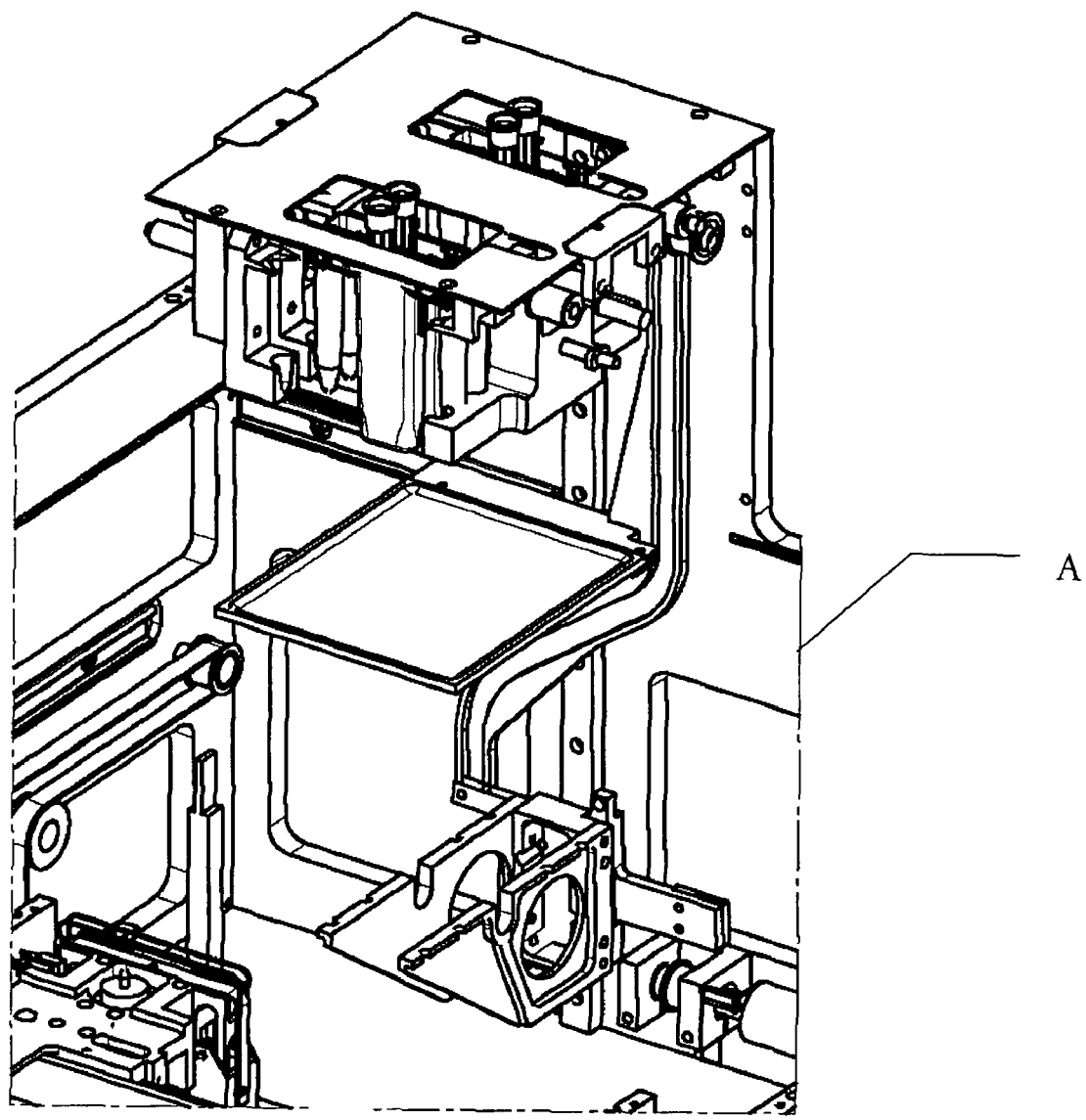
FIG. 7 shows cut-out A of the lift module in the status where four disposables (4) are placed in the input position on the second plain, the shutter is closed and the transfer module is ready for receiving disposables (4) in the output position (12) of the first plain (2).
Figure 8:
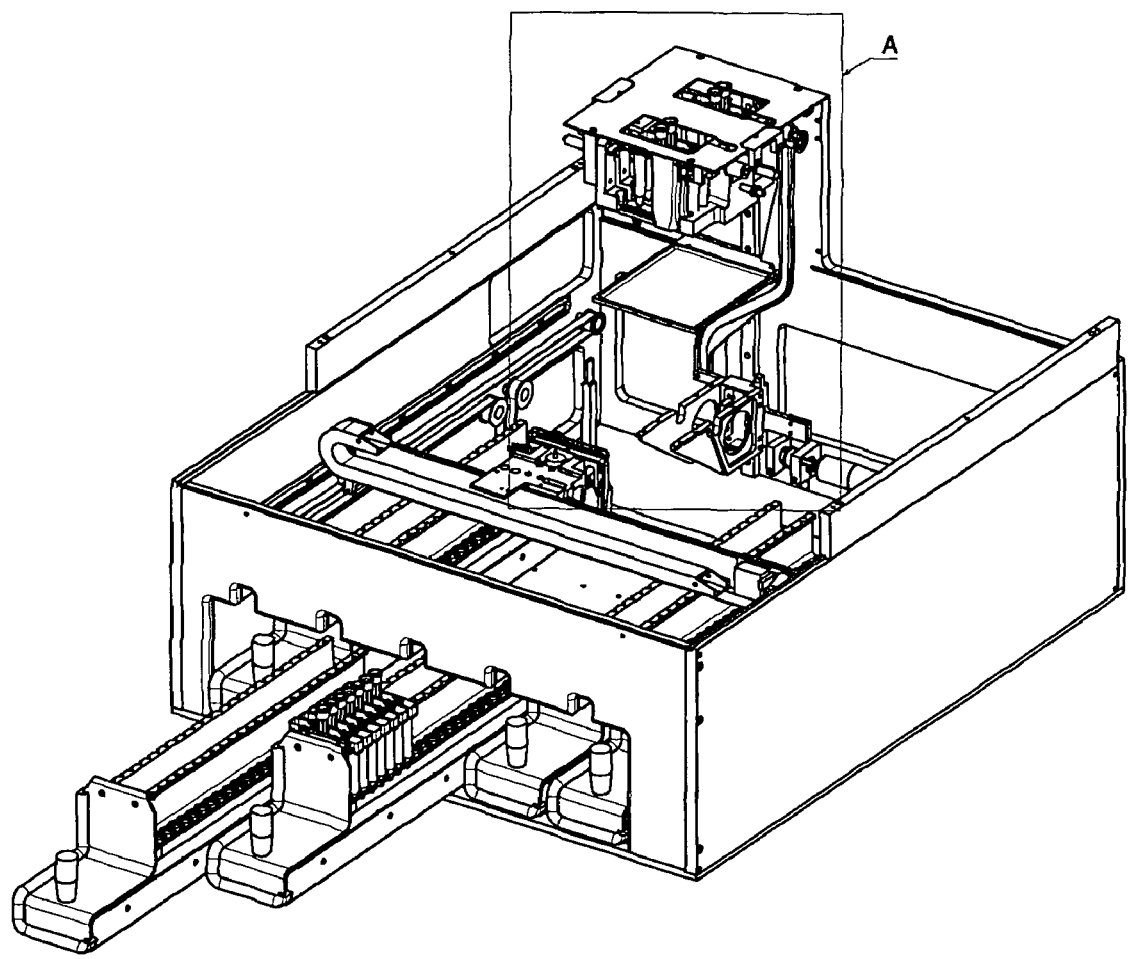
FIG. 8 shows the lift module of the apparatus from front and right hand side. A cut-out position is shown as A. The four disposables (4) are placed in the input position on the second plain (3), the shutter is closed and the transfer module is ready for receiving disposables in the output position (12) of the first plain (2).

Analytical processes are known. They frequently are multi-step process having two or more steps. Those steps can be performed in parallel or in a series. In the first case, a number of steps, same or different, are started at the same time. This is called the parallel mode. In the second case, the steps are performed in a series each at a different starting time. This is called the serial mode. In the preferred case, each series of steps is initiated at a different starting time. A very advantageous use of the present invention is found when serial and parallel mode of conducting steps is mixed. This is when performing several processes in parallel, each being composed of a series of subsequently performed steps. Those series of steps can be started at the same time or subsequently. Most preferred multi-step processes involve conducting the multistep procedure in parallel batches, for instance four series of processes are started at the same time, in parallel. After this first batch has undergone the first step and proceeds to the second step, the second batch of parallel processes is started, in the first step.

Analytical processes often require multiple steps during analysis of a sample. Therefore, analytical processes are the particular focus of use of the apparatus of the present invention. An example of such method is the analysis of a sample for a component, i.e. a chemical entity contained in the sample. Samples containing a large number of different components of interest are samples of natural origin. The samples can be solid or liquid. Examples of particular interest are body fluids or liquids derived therefrom. A particularly preferred liquid is blood or its derivatives, like serum and plasma. Further preferred liquids are urine and sputum. A solid sample is swab and tissue.

Analytical processes derive a result from analysis of a sample. Thus, the starting point of the analysis is a given amount of sample. The result mostly is provided as an electronic signal, shown on a display, for instance on a computer screen. While some analyses do not require chemical or mechanical treatment of the sample, most analyses include several steps of treating the sample, including releasing the components to be detected from their micro-environment in the sample, for example release of the component from cells they are associated with. Some analyses also require enrichment of the component to be detected. In another advantageous mode, preferred when other components of the sample interfere with the analysis, the component of interest is isolated and purified from the original sample and thereafter subjected to detection. Some steps of the procedure, like washing to remove impurities, may be repeated once or more times for a better result. The result typically is information given to the person doing the analysis, i.e. on a display, showing the fact of presence or the amount present of one or more components of the sample.

Typical analytical processes are clinical, immunological and molecular diagnostic analyses. Each of them requires multiple operational steps. Those steps are preferably selected from the group of adding or removing liquids or solids to the sample or any subsequently produced solids and liquids. Advantageously, those different steps for a number of reasons are done at different locations on the instrument. Those steps may therefore necessitate the transport of the sample or any derivatives thereof from one location to another on the instrument. In view of the fact that it is beneficial to do similar steps at one site and transport the sample as soon as new tools are needed, the steps are grouped together. In immunology, the procedure may comprise sample preparation, separation and detection. In nucleic acid analysis, the steps are preferably selected from the group consisting of sample preparation, amplification and detection. Each of these steps may be composed of complex subroutines.

Steps typically used in analyses are selected from the group of aspirating sample or/and reagents, dispensing sample or/and reagents, mixing sample or/and reagents, heating samples or/and reagents, picking up or/and releasing disposables or/and sample containers, discharging liquids or/and solids, irradiating items, detecting electromagnetic radiation and moving items.

The apparatus of the invention contains a storage of consumables and disposables needed for the analysis to be performed in the analysis and one or more waste containers for trash.

A plain according to the invention preferably is a flat region, a plane defined by two dimensions, i.e. a substantially planar region.

The apparatus according to the invention contains a first plain designed for storage of disposables. This plain is defined by a common area, where the desired number of disposables is stored, preferably all disposables being located on the same horizontal level. The plain can contain a number of containers (13) containing disposables, for instance in the form of drawers, on which the disposables are located. Such drawers may be advantageous for loading fresh disposables into the instrument according to the present invention. FIG. 1 show such drawers two of them being partially withdrawn from the instrument. Thus, the storage plain can be, but may not be a strict plain without interruption. Furthermore, the disposables or/and the containers (13) containing them can be held on storage means, for instance on one or more rails being on the same horizontal level.

The plain for storage of disposables, in the following called storage plain, may be equipped by a second transport module to transfer the disposables from one location on said plain to another location on said plain. This can be made by known means either effecting sliding of the disposables on rails or gripping the disposables, raising them, moving them to a place above the location to which they are intended to be transferred, and lowering them to said location. In FIG. 1, such transfer module can be seen clearly. The figure shows a transfer arm (6) movable along the rails (11) of the disposable containers and perpendicularly thereto, for reaching the four containers present in the first plain (2). Furthermore, the transfer means have a motor for driving the gripper to receive a disposable from the container, moving it to another position and placing it. Motors can be used also to drive other means, like heads and arms, for movement on rails or tracks.

For this reason, the storage plain comprises an area to which the disposables to be transferred are transported. This area is in the following called disposable output area.

The apparatus according to the invention further comprises a second plain, designed for processing said disposable. The term processing comprises the steps usually performed during analysis of a sample. Conveniently those steps are selected from one or more steps of the group of dispensing a sample into said disposable, adding reagents to said sample, removing parts of the sample from the disposable, and analyzing the liquid for any signal characteristic for the presence of the analyte. Those steps may be performed either in the disposable as provided from the storage plain or in other disposables or tubes into which the sample or liquids or solids derived therefrom are transferred.

The second plain, in the following called processing plain is located on a different horizontal level than the storage plain (i.e. it is not coplanar) and is substantially parallel to the first plain. The difference in height is preferably between 10 and 50 cm, more preferably between 15 and 40 cm. As the first plain, the second plain may not be completely planar, but may have elevated and decreased areas. On the process plain, preferably most of the processing steps in the analysis are performed. This second plain is partially shown in the figures as the plain where the elevator ends.

The processing plain comprises an area to which the disposables transferred from the storage plain are transported. This area is in then following called disposable input area.

In the apparatus of the invention, the first plain may comprise a region which is located above a region of the second plain, but preferably the second plain comprises a region which is located above a region of the first plain. In the first case, the disposables are lowered to the second plain, in the second case the disposables are raised to the second level. In the figures, the first plain is located below the second plain. Preferably, the lower region is smaller in dimension than the higher plain. The regions located above each other are in the following called overlapping regions. Preferably, the regions of overlap are the output area of the first plain and the input plain of the second plain. More preferably, the output area of the first plain is located above, most preferably perpendicular above, the input area of the second plain.

The transfer of the disposables from the first to the second plain is preferably done by an elevator. Elevators are generally known as means to for instance raise humans from one level to another level in a house, i.e. vertically. In automated analyses, elevators have not been used as there is a trend to maintain all subjects needed for analysis, i.e. reagents, samples and disposables, on a common working area. This may have been convenient to check whether all reagents and disposables are available in sufficient amount. This may have been sufficient for small disposables and small amounts of disposables. For large throughput instruments and for larger disposables, the working area does not provide sufficient space for storage. The invention has found that it is very convenient to store disposables at a different plain than the processing plain, if the apparatus is provided with a transfer module to transport the disposables from then storage plain to the processing plain as soon as needed.

The elevator according to the present invention is moving vertically, preferably on one or more rails or other guides, driven by a motor.

In a preferred embodiment, the disposables are transferred through a shaft or channel. Such channel is not shown in the figures. The invention provides means to close the channel when the channel is not needed for transport. This can easily be done by providing a shutter (5) in the channel that can be removed or withdrawn from the channel to allow transfer of the disposable. The shutter is very advantageous to avoid contamination of fresh disposables located in the storage plain by liquids handled in the processing plain, for instance when spilled through the aspiration or dispensing of liquid to the disposables in the processing plain. The shutter may be a plate sliding on one or more rails or other guides from a parking position into the channel. In another embodiment, the shutter is pivoted from a parking position into the channel. Conveniently, the shutter is inserted into the channel in a height between the height of the storage and the processing plain. The movement of the shutter may be controlled by a computer also controlling the transfer module, but preferably controlled mechanically by a forced guide bearing (8).

Disposables include vessels, pipette tips, caps or reagent bottles. Vessels and pipette tips are known to be useful tools for handling liquids, for example in pipetting apparatus. Both, vessels and pipette tips can be used to transport, to maintain or to mix liquids. Vessels are containers for maintaining liquids or solids, usually made of plastics. Pipette tips are devices having at least two openings, one to enter a liquid, and another to withdraw fluid through the device, such that the liquid is drawn into the device by applying a vacuum. By lowering the pressure in the device, liquid is released from the device. Pipette tips are used in the form of disposable plastics, particularly if the liquid to be aspirated and dispensed should not contaminate samples treated subsequently using the same apparatus. Preferentially, after usage, pipette tips are discarded by releasing them from a socket through which they were attached to the vacuum pumping device. In the present invention, disposables may be a combination of vessels and pipettes. The disposable may have one or more cavities to receive reagents, reaction mixtures and sample.

For handling reagents from a reagent container, reusable pipettes or needles can be used. Those pipettes are preferentially made from metal and may be washed with a washing liquid prior to subsequent use with other reagents. Pipetting apparatus are generally known in the art. Usually they contain a pump to apply a vacuum in a controlled manner.

The transfer can be made in any manner, generally by receiving, moving and releasing the disposable to be transferred. Preferably, more than one disposable is transferred in one run. In a preferred mode, between 2 and 24 disposables are transferred. They can be held individually, or can be held on a common device. In the figures, the elevator (1) carries four disposables (4) in one run.

In a preferred embodiment of the present invention, the second plain is designed to accommodate the samples to be analyzed and bring it into a form ready to be analyzed. Such module will in the following be called "sample receiving module". Preferably, it contains an area for accommodating reagents, which is called "reagent input area", an area for input of samples to be analyzed, called "sample input area" and the area containing disposables called "disposable input area". Furthermore, the module comprises an area which is accessible to the transfer head. This area is called "working area". All reagents, samples and disposables are provided in the sample receiving module manifold, particularly, there is sufficient supply of disposables to receive the intended number of aliquots of samples to be analyzed, including controls.

Generally, samples and controls are provided in primary containers in an amount sufficient to allow as many analyses as intended.

Another subject of the invention is a method for analysis of a sample in an instrument comprising the steps
  providing a disposable on a first plain
  transporting said disposable within said first plain to an output position,
  transferring said disposable to an input position of a second plain, and
  processing said disposable in said second plain.

A preferred method is described in the figures. However, the method can be performed using the general means as described for the instrument.

In a preferred embodiment of the method the transfer of the disposable is done by an elevator (1). Further in a preferred embodiment, the disposables are transferred within any of the plains by transfer means different from the elevator. This can include horizontal and vertical movement. In a preferred embodiment, the processing done in the second plain comprises dispensing the sample into said disposable or/and analyzing said sample. As pointed out above, the method preferably comprises raising said disposable from said first plain to said second plain. In another mode, the method comprises lowering said disposable from said first plain to said second plain.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes

REFERENCE NUMERALS

1 Transfer module (Elevator/Lift)
2 First plain
3 Second plain
4 Disposable
5 Shutter
6 Transfer arm
7 Transfer head
8 Forced guide bearing
9 Input position of second plain (3)
10 Rail of first plain (2)
11 Rail for transfer means
12 Output position of first plain (2)
13 Container for disposables
14 Rail for elevator (1)

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. An apparatus for being used in an analytical process comprising:
   a transfer module,
   a first plain, effective to store disposables,
   a second plain effective to load and process samples within said disposables, wherein
   said first plain and said second plain overlap at least partially, and,
   a shutter for closing the overlapping area partially or totally, wherein the movement of said shutter is controlled mechanically by a rail guide comprising a substantially S-shaped member defining a path, said substantially S-shaped member movably coupled to an elevator and configured to be guided along said path by the movement of said elevator, thereby controlling the movement of said shutter,
   wherein said first plain and said second plain are not coplanar and are substantially parallel, and wherein said transfer module is an elevator for transporting said disposables from said plain for storage to said plain for processing.

2. The apparatus according to claim 1, further comprising a second transfer module for transporting said disposables within said first plain for storage.

3. The apparatus of claim 1, wherein the movement of said shutter is controlled by a computer also controlling said elevator.

4. A method for analyzing samples using an apparatus, wherein the apparatus comprises:
   a transfer module,
   a first plain, effective to store disposables,
   a second plain effective to load and process samples within said disposables, wherein
   said first plain and said second plain overlap at least partially, and,
   a shutter for closing the overlapping area partially or totally, wherein the movement of said shutter is controlled mechanically by a rail guide comprising a substantially S-shaped member defining a path, said substantially S-shaped member movably coupled to an elevator and configured to be guided along said path by the movement of said elevator, thereby controlling the movement of said shutter,
   wherein said first plain and said second plain are not coplanar and are substantially parallel, and wherein said transfer module is an elevator for transporting said disposables from said plain for storage to said plain for processing;
   the method for analyzing samples comprising:
   providing a disposable on the first plain, effective to store disposables,
   transporting said disposable within said first plain to a transfer position,
   transferring said disposable to the second plain, effective to load and process samples with said disposables, and
   processing said disposable in said second plain.

5. The method of claim 4, wherein said transferring step is performed by an elevator.

6. The method of claim 4, wherein said processing step comprises transporting said disposable within said second plain.

7. The method of claim 4, wherein said processing step comprises dispensing the sample into said disposable.

8. The method of claim 4, wherein said processing step comprises analyzing said sample.

9. The method of claim 4, wherein said transferring step comprises raising said disposable from said first plain to said second plain.

10. The method of claim 4, wherein said processing step comprises lowering said disposable from said first plain to said second plain.

* * * * *